United States Patent
Hamilton (10) Patent No.: US 11,672,712 B2
(45) Date of Patent: Jun. 13, 2023

(54) MOBILE ANIMAL ONCOLOGY CLINIC

(71) Applicant: Private Veterinary Oncology Consulting, LLC, Lebanon, NJ (US)

(72) Inventor: Matthew J. Hamilton, Lebanon, NJ (US)

(73) Assignee: Private Veterinary Oncology Consulting, LLC, Lebanon, NJ (US)

( * ) Notice: Subject to any disclaimer, the term of this patent is extended or adjusted under 35 U.S.C. 154(b) by 490 days.

(21) Appl. No.: 16/846,743

(22) Filed: Apr. 13, 2020

(65) Prior Publication Data
US 2021/0315748 A1  Oct. 14, 2021

(51) Int. Cl.
| | |
|---|---|
| A61G 3/00 | (2006.01) |
| G06Q 50/30 | (2012.01) |
| A61B 6/00 | (2006.01) |
| A61D 3/00 | (2006.01) |
| A61G 13/10 | (2006.01) |
| A61D 7/00 | (2006.01) |
| B60P 3/36 | (2006.01) |

(52) U.S. Cl.
CPC ............. *A61G 3/001* (2013.01); *A61B 6/508* (2013.01); *A61D 3/00* (2013.01); *A61D 7/00* (2013.01); *A61G 13/105* (2013.01); *B60P 3/36* (2013.01); *G06Q 50/30* (2013.01)

(58) Field of Classification Search
CPC ................................ A61G 3/001; A61B 6/508
USPC ....................................................... 296/24.38
See application file for complete search history.

(56) References Cited

U.S. PATENT DOCUMENTS

| | | | | |
|---|---|---|---|---|
| 5,511,594 | A * | 4/1996 | Brennan ................... | A61J 3/00 53/425 |
| 6,625,252 | B2 * | 9/2003 | Mirabella .............. | A61G 3/001 378/102 |
| 7,347,472 | B2 * | 3/2008 | Pellegrin, Jr. .......... | G09B 23/28 434/262 |
| 8,657,354 | B2 * | 2/2014 | Pomper ................ | A61N 5/1001 250/493.1 |
| D880,782 | S * | 4/2020 | Lomis ......................... | D30/108 |
| 2007/0102946 | A1 * | 5/2007 | Blackwell ................ | E04H 3/08 296/24.38 |
| 2009/0268870 | A1 * | 10/2009 | Pomper .................... | B60P 3/14 378/65 |

(Continued)

OTHER PUBLICATIONS

Germfree, "Mobile Laboratories", availbable at https://www.germfree.com/category/product-lines/mobile-laboratories/ accessed on Oct. 28, 2020.

(Continued)

*Primary Examiner* — Joseph D. Pape
(74) *Attorney, Agent, or Firm* — Fox Rothschild LLP (57) ABSTRACT

Systems for providing oncological services to animals are provided. The system includes a transportation vehicle configured to be driven under its own power. The transportation vehicle includes an outer frame housing a plurality of rooms. The plurality of rooms includes an examination room configured to enable a medical professional to medically examine and perform medical diagnostic testing one or more animals, a chemotherapy treatment room configured to enable the medical professional to perform one or more oncological treatments on the one or more animals, and a changing room configured to enable the medical professional to don or doff personal protective equipment.

16 Claims, 4 Drawing Sheets

(56) References Cited

U.S. PATENT DOCUMENTS

2022/0142814 A1* 5/2022 Stegmann .............. A61F 7/007

OTHER PUBLICATIONS

Heska, "Cuattro Uno" available at https://www.heska.com/product/cuattro-uno/ accessed on Oct. 28, 2020.

* cited by examiner

MOBILE ANIMAL ONCOLOGY CLINIC

BACKGROUND

The present disclosure relates to oncology clinics and, in particular, to a mobile oncology clinic for the diagnoses and treatment of animals with cancer.

The study and treatment of cancer-related illnesses has been developed over many centuries and continues to be developed, with improved methods of diagnostics and treatment being continuously improved upon. This has greatly decreased the rates of mortality for people diagnosed with many cancer-related illnesses. However, cancer diagnoses are not isolated merely to human beings. Cancer has been diagnosed, studied, and treated in animals as well as humans for many years. In order to receive diagnosis and treatment, animals must, for the most part, travel or be transported to an oncological treatment facility. This transportation of the animals in need of medical care is unfortunately not always feasible.

Due to the unpredictability of animals, the costs associated with transporting animals, and the various sizes and shapes of the animals depending on species, breed, etc., it can be difficult, costly, or functionally impossible for an animal to be transported to an oncological treatment facility. Animals and their handlers, in these situations, are faced with the difficult realization that the animals will be unable to receive the necessary diagnoses and treatment plans necessary for maintaining or improving the health of the animals.

Given the medical diagnostic, testing, and treatment equipment necessary for the diagnoses and treatment of cancer-related illnesses in animals, a simple doctor's visit to the animal hospital would not suffice in effectively treating the animals. Rather, a full oncological clinic is necessary for the effective treatment of the animals. An oncological clinic that is capable of being transported to the location of the animals that are in need of care is thus optimal in some situations in view of at least the limitations discussed above. Therefore, for at least these reasons, a mobile veterinary oncological clinic for the diagnoses and safe treatment of animals is needed, particularly in remote and underserviced areas.

SUMMARY

According to an aspect of the present disclosure, a system for providing oncological services to animals is provided. The system includes a transportation vehicle configured to be driven under its own power. The transportation vehicle includes an outer frame housing a plurality of rooms. The plurality of rooms includes an examination room configured to enable a medical professional to medically examine and perform medical diagnostic testing one or more animals, and a specially designed chemotherapy treatment room configured to enable the medical professional to perform one or more oncological treatments safely on the one or more animals.

According to various embodiments of the present disclosure, the transportation vehicle further includes one or more fans configured to blow or move air out of the chemotherapy treatment room and the transportation vehicle, generating a negative pressure within the chemotherapy treatment room.

According to various embodiments of the present disclosure, the chemotherapy treatment room includes a treatment table for placing the one or more animals.

According to various embodiments of the present disclosure, the treatment table is a retractable treatment table configured to accommodate a variety of animal sized within the chemotherapy treatment room.

According to various embodiments of the present disclosure, the one or more oncological treatments include administration of chemotherapeutic agents.

According to various embodiments of the present disclosure, the transportation vehicle further includes a driving compartment and an engine.

According to various embodiments of the present disclosure, the chemotherapy treatment room includes a biosafety hood configured to filter air within itself and the chemotherapy treatment room. According to various embodiments, the bio safety hood is configured to vent air outside of the system.

According to various embodiments of the present disclosure, the biosafety hood is configured to decrease exposure to chemotherapeutic agents.

According to various embodiments of the present disclosure, the chemotherapy treatment room includes one or more refrigeration containers. According to various embodiments, the one or more refrigeration containers are dedicated refrigeration containers configured to house one or more objects/materials pertaining to one or more chemotherapy treatments. According to various embodiments, the dedicated refrigeration containers are secured in place within the transportation vehicle or may be movable within the transportation vehicle.

According to various embodiments of the present disclosure, one or more of the plurality of rooms includes a sink. The sink may be hooked up to an internal water source such as that within a tank or connected to an external water source. According to various embodiments, the sink is positioned approximately 1 meter or more from the biosafety room. According to various embodiments, biosafety hood is 1 meter or farther from a water source. According to various embodiments, if the biosafety hood cannot be 1 meter or farther from a water source, the water source needs to be in another room (for example, the donning and doffing room).

According to various embodiments of the present disclosure, the transportation device includes a water tank coupled to the sink.

According to various embodiments of the present disclosure, the plurality of rooms further includes a changing room for donning and doffing of personal protective equipment. According to various embodiments, the changing room is configured to enable the medical professional to prepare to perform the one or more oncological treatments on the one or more animals.

According to various embodiments of the present disclosure, the examination room includes a plurality of cabinets and an examination table.

According to various embodiments of the present disclosure, the examination room includes one or more animal storage containers configured to safely house one or more animals.

According to various embodiments of the present disclosure, the transportation vehicle includes a generator configured to power one or more components of the transportation device.

According to various embodiments of the present disclosure, the transportation vehicle includes one or more imaging devices.

According to various embodiments of the present disclosure, the one or more imaging devices includes an x-ray machine configured to image portions of the one or more animals. According to various embodiments, the transportation vehicle may include other forms of imaging devices such as, for example, ultrasound imaging devices.

According to various embodiments of the present disclosure, the one or more imaging devices are positioned in the examination room.

According to various embodiments of the present disclosure, the transportation vehicle includes a two-way fan configured to adjust air pressure within the examination room. The two-way fan may be configured to expel air from, or blow air into, the transportation vehicle, depending on the direction and position of the two-way fan.

According to various embodiments of the present disclosure, the outer frame includes an entryway from outside of the transportation vehicle to one or more of the plurality of rooms.

According to various embodiments of the present disclosure, the transportation vehicle includes one or more air conditioners configured to regulate temperature within one or more of the plurality of rooms.

DETAILED DESCRIPTION

As used in this document, the singular forms "a," "an," and "the" include plural references unless the context clearly dictates otherwise. Unless defined otherwise, all technical and scientific terms used herein have the same meanings as commonly understood by one of ordinary skill in the art. When used in this document, the term "comprising" (or "comprises") means "including (or includes), but not limited to." When used in this document, the term "exemplary" is intended to mean "by way of example" and is not intended to indicate that a particular exemplary item is preferred or required.

In this document, when terms such "first" and "second" are used to modify a noun, such use is simply intended to distinguish one item from another, and is not intended to require a sequential order unless specifically stated. The term "approximately," when used in connection with a numeric value, is intended to include values that are close to, but not exactly, the number. For example, in some embodiments, the term "approximately" may include values that are within +/−10 percent of the value.

Other terms that are relevant to this disclosure are defined at the end of this Detailed Description section.

Figure 1:
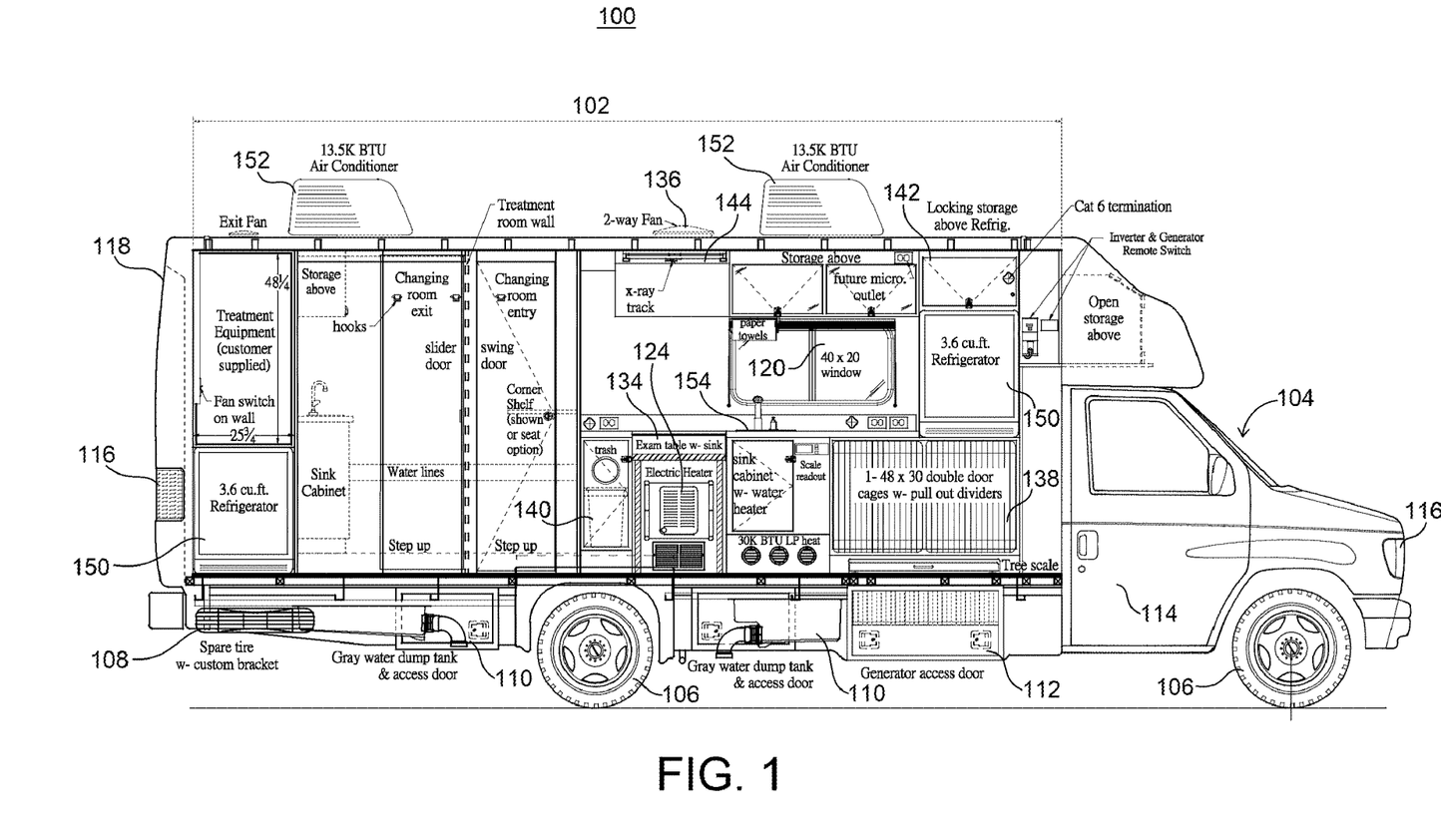
FIG. 1 is a driver side schematic view of a mobile animal oncology clinic, in accordance with various embodiments of the present disclosure.
Figure 2:
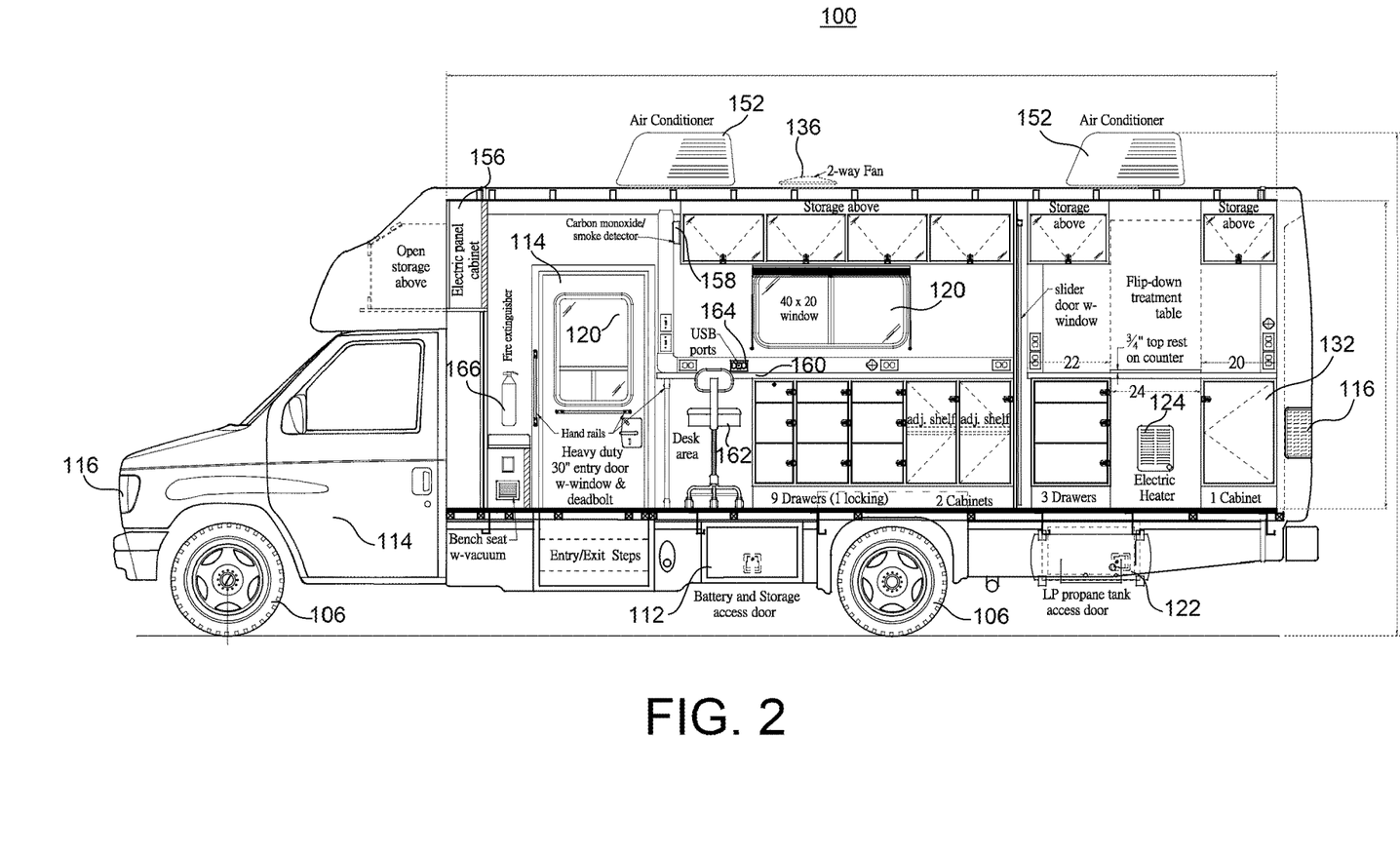
FIG. 2 is a passenger side schematic view of a mobile animal oncology clinic, in accordance with various embodiments of the present disclosure.
Figure 3:
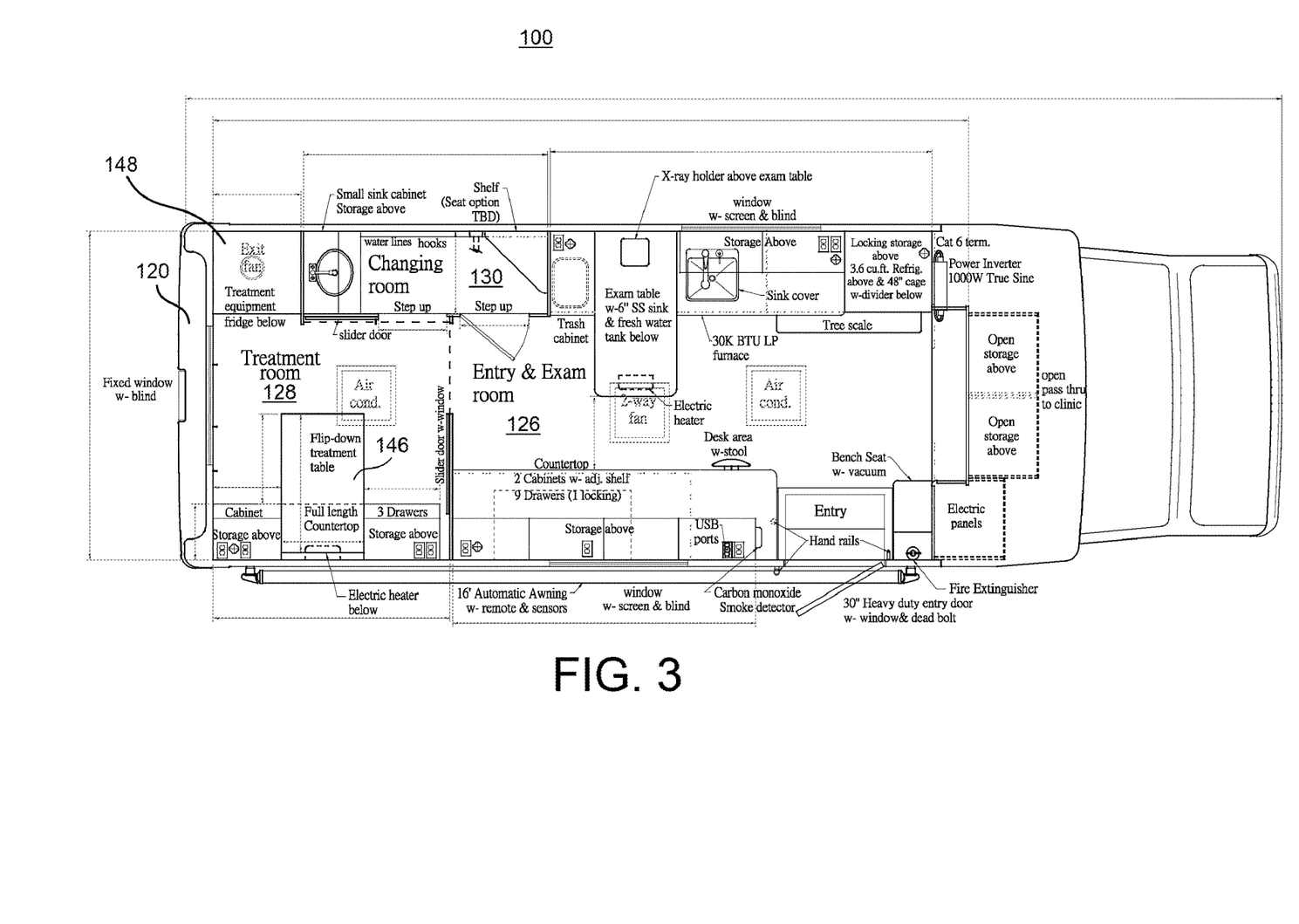
FIG. 3 is a top schematic view of a mobile animal oncology clinic, in accordance with various embodiments of the present disclosure.
Figure 4:
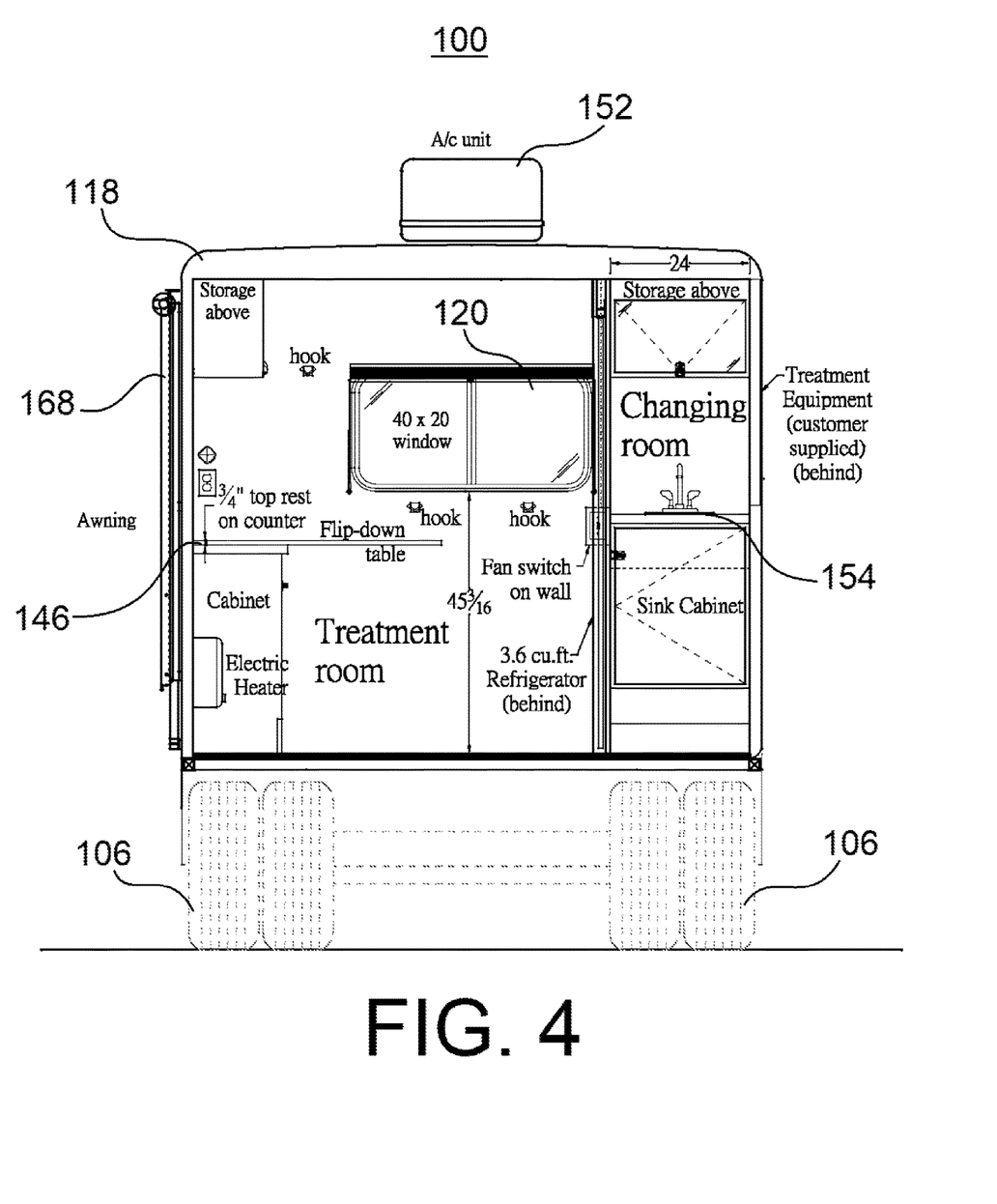
FIG. 4 is a rear schematic view of a mobile animal oncology clinic, in accordance with various embodiments of the present disclosure.

Referring now to FIGS. 1-4, a driver side schematic view (FIG. 1), a passenger side schematic view (FIG. 2), a top schematic view (FIG. 3), and a rear schematic view (FIG. 4) of a mobile system 100 for providing oncological services to animals is provided, according to various embodiments of the present disclosure.

According to various embodiments, the mobile system 100 forms a mobile oncological clinic enabling medical professionals to transport the mobile system 100 to one or more distinct locations to provide oncological services which includes, for example, diagnostics, examination, testing, treatment (for example, chemotherapy treatment), and/or any other suitable oncological services to one or more animals suitable for receiving the services provided by the mobile system 100.

Due to the sometimes difficult, dangerous, and costly process for transporting animals, animal handlers are often incapable of transporting animals to locating where oncological treatments are being provided. This results in these animals failing to receive the diagnostic procedures, examinations, and oncological treatments necessary for the health and well-being of the animals. This problem only increases in areas that are remote and/or underserviced by veterinary medical professionals. The present mobile system 100, by being capable of transporting the animal oncology clinic to the animals, increases the number of animals capable of being treated without having to deal with the difficulties, dangers, and costs associated with the transportation of animals, let alone unhealthy animals in need of medical care.

The mobile system 100, either by moving under its own power or by being towed by an external vehicle, has the capability of bringing the diagnostic and treatment facility directly to the animal. Depending upon the length of a treatment session and the proximity of multiple animals in need of medical care to each other, in a single day or on a single trip, multiple animals can receive suitable and possibly life-saving medical care, due to the mobility of the mobile system 100.

According to various embodiments, the mobile system 100 is a transportation vehicle and includes a self-contained oncological clinic compartment 102, the self-contained oncological treatment area compartment 102 being configured to enable a medical professional to provide diagnostic testing, medical examination, and medical treatment within the self-contained oncological treatment area compartment 102. According to various embodiments, the self-contained oncological treatment area compartment 102 includes equipment and/or medication which may be administered outside of the mobile device 100. For example, the self-contained oncological treatment area compartment 102 may include may include the tools necessary for drawing blood and/or administering medication to an animal which cannot safely be brought inside the self-contained oncological treatment area compartment 102, such a, for example, a horse or other large animal.

In order to transport the mobile system 100, the mobile system 100 may further include a driving compartment 104, which may include systems and/or mechanisms for controlling the movement of the mobile system 100, such as, for example, steering mechanisms, propulsion control mechanisms, and/or any other suitable driving mechanisms configured to enable a user to transport the mobile system 100. The mobile system 100 may further include one or more systems and/or mechanisms for propelling the mobile system 100, such as, for example, an engine, one or more fuel compartments or battery compartments for powering the transportation of the mobile system, one or more fuel exhaust systems, a plurality of wheels 106, and/or any other devices configured to aid in the propulsion of the mobile system 100.

Many of the devices in the mobile system 100 may run on electricity. According to various embodiments, the mobile system 100 may include one or more power supplies 112

(e.g., electricity generators, batteries, etc.) configured to power one or more devices housed within, or coupled to, the mobile system 100. The mobile system 100 may further include one or more control panels 156 for controlling one or more electrical functions of the mobile system 100. The mobile system 100 may further, or alternatively, include a power receiving port configured to enable an outside power source to power one or more components of the mobile system 100.

It is noted that the mobile system 100 may include one or more systems, devices, and/or mechanisms typically used in conjunction with automobiles or recreational vehicles, such as, for example, one or more spare tires 108, one or more water tanks 110, one or more entrance/exit doors 114, one or more external lights 116, an outer frame 118, one or more windows 120, one or more propane tanks 122, one or more heaters 124, one or more air conditioners 152, and/or any other suitable systems, devices, and/or mechanisms typically used in conjunction with automobiles or recreational vehicles. According to some embodiments, the outer frame 118 may have an electric and/or manual awning 168 coupled thereto.

According to various embodiments, the mobile system 100 is of a suitable size such that the mobile system 100 can be transported under its own power and does not require towing or any other form of external propulsion from a separate propulsion device such as, for example, a towing vehicle, an aircraft, a watercraft, etc. According to other various embodiments, the mobile system 100 is configured to be towed by a secondary vehicle. According to various embodiments of the present disclosure, the mobile system 100 has a length of approximately 18-35 feet. However, it is noted that the length of the mobile system 100 may be any suitable length while maintaining the spirit of the mobile system 100.

The mobile system 100 includes an outer housing 118. The outer housing is configured to house one or more components of the mobile system 100. According to various embodiments, the outer housing 118 is configured to house a plurality of rooms within the mobile system 100 and, in particular, within the self-contained oncological treatment area compartment 102. According to some embodiments, the outer housing 118 is further configured to house the driving compartment 104.

Depending on the means of the medical diagnostic testing, medical examinations, and/or medical treatment procedures, one or more harmful substances may be used and/or created. According to various embodiments, in order to prevent or reduce the escape of these potentially dangerous substances and materials, the mobile housing 118 may be configured to include one or more materials which are configured to aid in the prevention of certain toxic compounds and/or any other similar compounds and/or compounds which pose a pollution risk, from penetrating the mobile housing 118.

According to various embodiments, the housing 118 houses a plurality of rooms within the mobile system 100 in the self-contained oncological treatment area compartment 102. The plurality of rooms may include an examination room 126, a chemotherapy treatment room 128, a changing room 130, and/or any other suitable rooms for the examination, diagnosis, and/or oncological treatment of animals. An example of the size and location of these rooms is shown at least in FIG. 3. However, it is noted that the size, shape, and position of these rooms within the self-contained oncological treatment area compartment 102 may be altered while still maintaining the spirit and functionality of the mobile system 100. Additionally, while the mobile system 100 is described as used for the performance of oncological services on animals, it is noted that the mobile system 100 may, according to some embodiments, be used for the administration of non-oncological medical services in conjunction with, or instead of, oncological medical services.

According to various embodiments, the examination room 126 is configured to enable a medical professional to medically examine one or more animals and/or perform medical diagnostic testing on the one or more animals. According to various embodiments, the mobile system 100 has an entryway (for example, a door) which enables a user and/or an animal to enter the mobile system 100 and enter into the examination room 126. The examination room 126 may include one or more cabinets 132, drawers 142, waste receptacles 140, and/or any other suitable compartment for the storing/housing of medical equipment, testing equipment, safety equipment, medications, and/or any other items which may suitably need to be housed within the examination room 126.

The examination room may further include one or more treatment tables 134 configured to enable one or more animals to be placed upon the one or more treatment tables, aiding in the examination of the one or more animals. The one or more treatment tables 134 may be in a permanent position or may be retractable, enabling the one or more treatment tables 134 to be moved for safe storage and to increase the available room within the examination room 126, due to the limited amount of space available within the mobile system 100. The examination room may further include one or more two-way fans 136 configured to draw in and blow air out of the examination room 126, enabling the pressure within the examination room 126 to be adjusted. The fans 136 may be configured such that air blown through the fans is expelled from the mobile system 100. The examination room 126 may further be equipped with one or more desks 160 and/or one or more seating devices 162. For the powering of equipment, the examination room 126 may additionally be equipped with one or more power stations 164 (e.g., USB ports, power outlets, etc.).

The safety of the medical professional and the animal is of utmost importance within the examination room 126. To aid in maintaining the safety of the medical professional and of the animal, the examination room 126 may be equipped with one or more animal storage compartments 138. Additionally, one or more safety sensors 158 (e.g., smoke detectors, carbon monoxide detectors, explosive gas detectors, etc.) and/or fire extinguishers 166 may also be installed within the mobile system 100.

Imaging equipment and techniques may be used in the diagnosis and examination of the one or more animals in the examination room 126. For example, according to various embodiments, the examination room includes an x-ray imaging machine 144 for imaging one or more portions of the one or more animals being examined in the examination room 126. According to various embodiments, the x-ray imaging equipment 144 is hung from the ceiling in the examination room 126. It is noted, however, that any suitable method of securing the x-ray imaging equipment 144 may be incorporated while maintaining the spirit of the mobile system 100. It is further noted that other forms of imaging equipment such as, for example, ultrasound imaging equipment, may be incorporated within the mobile system 100. Additionally, it is noted that one or more of the devices present in the mobile system 100 may be in electronic communication with one or more other devices present in the mobile system 100. One or more devices present within the mobile system 100 may also be in electronic communication with one or more devices not present in the mobile system 100.

The chemotherapy treatment room 128 is configured to enable one or more medical professionals to perform one or more medical treatments on the one or more animals. According to various embodiments, the one or more medical treatments are oncological medical treatments, although non-oncological medical treatments may, additionally or alternatively, be performed by the medical professional in the chemotherapy treatment room 128. The chemotherapy treatment room 128 may include one or more cabinets 132, drawers 142, waste receptacles 140, and/or any other suitable compartment for the storing/housing of medical equipment, testing equipment, safety equipment, medications, and/or any other items which may suitably need to be housed within the chemotherapy treatment room 128. The chemotherapy treatment room 128 may include one or more treatment tables 146 for the placement of one or more animals receiving medical treatment.

In order to maintain a satisfactory level of safety within the chemotherapy treatment room 128, the chemotherapy treatment room 128 may be equipped with a biosafety hood 148 configured to aid in the prevention of the escape of hazardous materials which may be used during oncological treatments. According to various embodiments, the biosafety hood 148 is a chemotherapy hood configured to decrease exposure to chemotherapeutic agents which may be used during the administration of oncological treatments on the one or more animals. According to various embodiments, the biosafety hood 148 may be configured to vent air out of the mobile system 100. The chemotherapy hood 148 may be positioned in a corner of the chemotherapy treatment room 128 in order to allow the venting of air that has been filtered out of the mobile system 100.

According to various embodiments, the chemotherapy treatment room 128 includes a refrigerator 150 which may be a dedicated chemotherapy refrigerator configured to house one or more objects/materials pertaining to one or more chemotherapy treatments. Other rooms in the mobile system 100, e.g., the examination room 126, may additionally, or alternatively, include refrigerators 150. The dedicated chemotherapy refrigerator 150 may be positioned under the chemotherapy hood 148, although other positional configurations may also, or alternatively, be implemented. The treatment table 146 may be in a permanent position or may be retractable, enabling the treatment table 146 to be moved for safe storage and to increase the available room within the chemotherapy treatment room 128. According to various embodiments, the treatment table 146 may be configured to accommodate a variety of animal sizes in the chemotherapy treatment room 128.

According to various embodiments, the mobile system 100 includes one or more fans coupled to the housing, which are configured to blow or move air out of the chemotherapy treatment room 128 and/or out of the mobile system 100 faster than air can enter the chemotherapy treatment room and/or the mobile system 100. This causes a negative pressure to be generated within the chemotherapy treatment room 128, which aids in the prevention of any harmful compounds from leaking out of the chemotherapy treatment room 128 and into other one or more other rooms, compartments, and/or other storage devices, such as refrigeration units/containers, within the mobile system 100, helping maintain a level of safety within the mobile system 100 during use.

According to various embodiments, the chemotherapy treatment room 128 is configured to enable one or more medical professionals to perform one or more oncological treatments on one or more animals. The one or more oncological treatments may include, for example, the administration of chemotherapeutic agents. Other forms of oncological treatment may also be performed within the chemotherapy treatment room 128, and the chemotherapy treatment room 128 may be configured to aid in the performance of those treatments. Additionally, while the mobile system 100 is described as being configured for aiding in the performance of oncological services on animals, it is noted that the mobile system 100 may, according to some embodiments, be used for the administration of non-oncological medical services in conjunction with, or instead of, oncological services. For example, the imaging devices, such as the x-ray imaging device, may be used by medical professionals to diagnose and treat broken bones.

In addition to aiding medical professionals in performing medical procedures, the mobile system 100 is further configured to aid the medical professionals in preparing to perform medical treatments. Prior to the performance of medical procedures, the medical professional or professionals must adequately prepare themselves. The changing room 130 is configured to enable medical professionals to prepare to perform one or more oncological treatments and/or any other suitable form of medical treatment on the one or more animals being treated. The changing room 130 may further be configured to enable medical professionals to don and/or doff any personal protective equipment prior to performing any medical procedures.

According to various embodiments, one or more of the plurality of rooms has access to running water and/or may include a sink 154 or a plurality of sinks 154. According to various embodiments, the sink 154 is positioned 1 meter or farther from the bio safety hood 148. According to various embodiments, biosafety hood 148 is 1 meter or farther from a water source. According to various embodiments, if the biosafety hood 148 cannot be 1 meter or farther from a water source, the water source needs to be in another room (for example, the changing room 130).

The water may be accessed from an external water hookup and/or may be accessed from one or more water storage containers (for example, a water tank) housed within the mobile system 100. The ability to access flowing water aids in the disinfecting of any people, animals, and/or objects that may enter the mobile system 100.

In this document, "electronic communication" refers to the transmission of data via one or more signals between two or more electronic devices, whether through a wired or wireless network, and whether directly or indirectly via one or more intermediary devices. Devices are "communicatively connected" if the devices are able to send and/or receive data via electronic communication.

The features and functions described above, as well as alternatives, may be combined into many other different systems or applications. Various alternatives, modifications, variations or improvements may be made by those skilled in the art, each of which is also intended to be encompassed by the disclosed embodiments.

The invention claimed is:

1. A system for providing oncological services to animals, comprising:
   a transportation vehicle configured to be driven under its own power, comprising:
   an outer frame housing a plurality of rooms, the plurality of rooms comprising:

an examination room configured to enable a medical professional to medically examine and perform medical diagnostic testing one or more animals, wherein the examination room comprises:
an exam table:
one or more two-way fans configured to draw in and blow air out of the examination room, enabling a pressure within the examination room to be adjusted;
a chemotherapy treatment room configured to enable the medical professional to perform one or more oncological treatments on the one or more animals, wherein the chemotherapy treatment room comprises:
one or more treatment tables; and
a biosafety hood configured to:
filter air within the chemotherapy treatment room,
generating filtered air; and
vent the filtered air out of the transportation vehicle; and
a changing room configured to enable the medical professional to don or doff personal protective equipment; and
one or more fans configured to blow or move air out of the chemotherapy treatment room and the transportation vehicle, generating a negative pressure within the chemotherapy treatment room.

2. The system as recited in claim 1, wherein the one or more treatment tables comprise a retractable treatment table.

3. The system as recited in claim 1, wherein the one or more oncological treatments comprise administration of chemotherapeutic agents.

4. The system as recited in claim 1, wherein the biosafety hood comprises a chemotherapy hood configured to decrease exposure to chemotherapeutic agents during administration of oncological treatments.

5. The system as recited in claim 1, wherein the transportation vehicle further comprises:
a driving compartment; and
an engine.

6. The system as recited in claim 1, wherein the chemotherapy treatment room comprises one or more refrigeration containers.

7. The system as recited in claim 1, wherein one or more of the plurality of rooms comprises a sink.

8. The system as recited in claim 7, wherein the transportation device comprises a water tank coupled to the sink.

9. The system as recited in claim 1, wherein the examination room comprises:
a plurality of cabinets; and
an examination table.

10. The system as recited in claim 1, wherein the examination room comprises one or more animal storage containers configured to safely house one or more animals.

11. The system as recited in claim 1, wherein the transportation vehicle comprises a generator configured to power one or more components of the transportation device.

12. The system as recited in claim 1, wherein the transportation vehicle comprises one or more imaging devices.

13. The system as recited in claim 12, wherein the one or more imaging devices comprises an x-ray machine configured to image portions of the one or more animals.

14. The system as recited in claim 12, wherein the one or more imaging devices are positioned in the examination room.

15. The system as recited in claim 1, wherein the outer frame comprises an entryway from outside of the transportation vehicle to one or more of the plurality of rooms.

16. The system as recited in claim 1, wherein the transportation vehicle comprises one or more air conditioners configured to regulate temperature within one or more of the plurality of rooms.

* * * * *